(12) United States Patent
Irion et al.

(10) Patent No.: US 6,510,338 B1
(45) Date of Patent: Jan. 21, 2003

(54) METHOD OF AND DEVICES FOR FLUORESCENCE DIAGNOSIS OF TISSUE, PARTICULARLY BY ENDOSCOPY

(75) Inventors: Klaus M. Irion, Liptingen (DE); André Erhardt, Tuttlingen (DE); Herbert Stepp, Planegg (DE); Josef Peter Pichler, Irschenberg (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/633,696

(22) Filed: Aug. 7, 2000

Related U.S. Application Data

(63) Continuation of application No. PCT/DE99/00340, filed on Aug. 2, 1999.

(30) Foreign Application Priority Data

Feb. 7, 1998 (DE) ........................................ 198 04 797

(51) Int. Cl.[7] .............................. A61B 5/00; A61B 6/00
(52) U.S. Cl. .................. 600/476; 600/478; 600/160
(58) Field of Search ................................. 600/476, 473, 600/478, 160, 178, 181, 109; 250/458.1, 461.2, 462.1; 356/317, 318

(56) References Cited

U.S. PATENT DOCUMENTS

| | | | |
|---|---|---|---|
| 5,413,108 A | * 5/1995 | Alfano | 600/478 |
| 5,701,903 A | * 12/1997 | Sano et al. | 600/478 |
| 5,769,792 A | * 6/1998 | Palcic et al. | 600/477 |
| 5,833,617 A | * 11/1998 | Hayashi | 600/476 |
| 5,971,918 A | * 10/1999 | Zanger | 600/160 |
| 6,110,106 A | * 8/2000 | MacKinnon et al. | 600/181 |
| 6,128,525 A | * 10/2000 | Zeng et al. | 600/476 |
| 6,148,227 A | * 11/2000 | Wagnieres et al. | 600/476 |
| 6,212,425 B1 | * 4/2001 | Irion et al. | 600/476 |
| 6,217,510 B1 | * 4/2001 | Ozawa et al. | 600/129 |
| 6,422,994 B1 | * 7/2002 | Kaneko et al. | 600/160 |

FOREIGN PATENT DOCUMENTS

| | | |
|---|---|---|
| DE | 41 33 493 A1 | 4/1992 |
| DE | 196 12 536 A1 | 10/1997 |
| EP | 512 965 A1 | 5/1992 |
| WO | WO 97/11636 | 4/1997 |

OTHER PUBLICATIONS

Endoworld D–Light by Karl Storz GmbH & Co. This article will follow.

* cited by examiner

Primary Examiner—Shawna J Shaw
(74) Attorney, Agent, or Firm—St. Onge Steward Johnston & Reens LLC

(57) ABSTRACT

A method of and a device for the endoscopic fluorescence diagnosis of tissue, wherein the tissue is exposed to stimulating light via an endoscope for stimulation of fluorescence, which stimulating light is suitable, on account of its spectral distribution, to stimulate at least two different fluorescence modes in the tissue without filter switching in the stimulation beam path, and wherein the fluorescence light of the different fluorescence modes can be selectively observed.

66 Claims, 1 Drawing Sheet

METHOD OF AND DEVICES FOR FLUORESCENCE DIAGNOSIS OF TISSUE, PARTICULARLY BY ENDOSCOPY

CROSS REFERENCE TO PENDING APPLICATION

This application is a continuation of pending International application PCT/DE99/00340 filed Feb 8, 1999 which designated the United States.

DESCRIPTION

FIELD OF THE INVENTION

The present invention relates to a method of fluorescence diagnosis of tissue, particularly by endoscopy, as well as devices for performing fluorescence diagnoses. Such devices are also referred to as photodynamic diagnosis systems (PDD systems).

These methods or devices, respectively, are employed for the "in vivo" diagnosis operating on a reaction induced by light in biologic tissue by an endogenic or exogenic photo sensitising agent; such methods and devices can be employed in particular for the (early) diagnosis of tumours and for tumour localisation.

Fundamentals

For triggering a light-induced reaction in biologic systems a photo sensitising agent (also referred to as photo sensitizer) can be administered to the patient in a concentration of a few mg/kg of the body weight. Typical photo sensitizers display a basic hemato-porphyrin structure such as the substances Photofrin and Photosan-3. Another photo sensitizer that is frequently used in urology and dermatology is delta amino levulinic acid (ALA).

The hemato-porphyrin derivatives are administered into the veins whereas delta amino levulinic acid is suitable for local application, which means that it is injected as a solution into the urinary bladder. These substances accumulate in tumour tissues in a concentration increased by 2 to 10 times. This selective accumulation in the tumour tissue constitutes the decisive basis for diagnosing tumours by photo dynamic diagnosis and for the photo dynamic tumour therapy.

For diagnosis, the tissue to be examined is exposed to ultraviolet irradiation for roughly 2 to 12 hours after administration of the photo sensitizer. The photo-sensitising agents present in the tumour tissue in an increased concentration are stimulated by this light and present thereafter a typical red fluorescence by which the tumour can be localised.

In addition to fluorescence—induced by a photo sensitizer accumulated in the tissue—also the so-called auto fluorescence can be triggered in the tissue, which is brought about by so-called fluorophores, i.e. endogenic fluorescent substances.

The bio-physical sequence of light-induced reaction can be assumed to develop as follows:

The photo sensitizer accumulated in the tissue is caused to switch over into an excited state by the absorption of a light quantum carrying a defined energy, which is emitted by the respective light source. Exposure to violet light as part of the photo dynamic diagnosis causes the emission of a fluorescent radiation when the sensitizer returns into the basic state.

In the case of photo dynamic therapy in combination with irradiation with red light at a high power density the transition takes place from the excited state into a meta stable interim state from which the energy that is discharged by the return into the basic state is transferred to molecular oxygen which receives this energy and forms thereby stimulated singlet oxygen. The aggressive singlet oxygen destroys cell structures in the respective tissue by photo oxidation. This cellular damage, together with a simultaneously occurring collapse of the tumour vessel system, results in a complete destruction of the tumour (photo toxic effect).

Prior Art

A method and a device which the wording of the independent Patent Claims starts out from is known from the document WO 97/11636 or the pamphlet "Endoworld D-Light" by Karl Storz GmbH & Co.

PDD systems of another general type are disclosed in the German Patent DE-A41 33 493 or the U.S. Pat. No. 5,701,903. Moreover, the realisation of an endoscopic photo dynamic diagnosis and therapy by means of a device has been proposed wherein a laser, specifically a krypton ion laser, is employed as light source emitting a wavelength of roughly 420 nm and producing a power of more than 200 mWatt. The light of this laser is passed via an optical quartz guide having a numerically small aperture through an endoscope to the locations in the human body which are to be irradiated.

For an explanation of all particulars not described here in details explicit reference is made, by the way, to the aforementioned prior art documents.

The "D-Light system" described in the aforementioned pamphlet has been designed for application with 5-amino levulinic acid (5-ALA) as photo sensitizer also for the induced fluorescence analysis.

For such an application the device comprises an illuminating system including at least one illuminating light source which emits a stimulating light over a wide bandwidth for stimulating the fluorescence of the photo sensitizer. The light is coupled into the optical guide of an endoscope including a lens with an object field illuminated by the stimulating light, and an image transmitting system which transmits the image from the lens to the proximal end of the endoscope. Moreover, a filter system is provided that comprises stimulating filters in the light path between the illuminating system and the tissue to be examined, as well as observation filters along the path of the observation beams, as formed by the lens and the image transmitting system. The characteristics of the stimulating filter in transmission are so selected that the spectral distribution of the stimulating light is matched with the fluorescence stimulating spectrum of the tissue to be examined. The transmission characteristics of the observation filter are so selected that, on the one hand, the fluorescent light is not outshone by the stimulating light reflected on the tissue directly but that, on the other hand, the area under examination can also be observed by the examining physician also due to the directly reflected stimulating light.

The known PDD system "D-Light" has been applied in urology, neuro surgery and other branches for photo dynamic diagnosis with great success.

On the other hand, lung cancer is the most frequently occurring cause of death due to cancer. Attempts have been made to administer the photo sensitizer 5-ALA by inhalation. This furnishes good results only partly. What is particularly problematic is the reproducibility of this form of administration. In accordance with the invention, now the fact has been detected that this problem can be overcome by the simultaneous detection of auto fluorescence.

All the methods in which fluorescence is induced by means of a photo sensitizer suffer from the further advantage that preliminarily the photo sensitizer(s) must be administered for producing its or their effects only after a certain time—within the range from several minutes to a couple of hours—which, on the other hand, is (are) bleached out in the course of the examination and might also be intolerable under certain conditions.

For this reason methods have been proposed which utilise only the auto fluorescence of tissue. Appropriate systems are disclosed, for instance, in the European Patent EP-B-0 512 965, the U.S. Pat. No. 5,507,287, the U.S. Pat. No. 5,413,108, or the German Patent DE-A-196 461 776. What is a disadvantage in these methods is the aspect that they employ merely the auto fluorescence effect for diagnosis—even though they are comparatively expensive—and hence furnish a comparatively low-contrast image in many cases.

All the aforementioned systems share the common feature that the filter systems provided in the path of the illuminating beams or the observation beams, respectively, are matched with the type of the respective fluorescence to be stimulated. As a consequence, it is necessary to change the filters when fluorescence is stimulated by means of another photo sensitizer or when a change is to be made from fluorescence induced by a photo sensitizer or auto fluorescence.

BRIEF DESCRIPTION OF THE INVENTION

The present invention is based on the problem of providing a method of endoscopic fluorescence diagnosis of tissue, which permits the execution of different diagnostic procedures—i.e. diagnostic procedure operating on different photo sensitizers and/or of induced and endogenic fluorescence; moreover, the inventive device should be so designed that the expenditure incurred by a conversion of the device to different diagnostic procedures will be reduced against known devices.

Inventive solutions to this problem are defined in the independent Patent Claims. Improvements of the invention are the subject matters of the dependent Claims.

In accordance with the invention the transmission characteristics of the stimulating filter or filters are so selected that on account of its spectral distribution the stimulating light is able to stimulate at least two different fluorescence modes in the tissue without switching the stimulating filters. The light emitted from the illuminated or irradiated tissue, respectively, due to the at least two different fluorescence modes is selectively observed:

It is possible, for instance, to detect the light, that is emitted from the tissue, as a function of the wavelength; in this approach the following—exemplary and not limiting—procedure is conceivable:

1. Initially, the light emitted from the tissue in one or several wave length bands is detected—if applicable with inclusion of auto fluorescence.
2. After administration of one or several photo sensitizer(s) the way is detected in which the emission varies within the wave length bands typical of the fluorescence of these photo sensitizers.
3. In this method it is possible to detect in particular the variation of the emission in this wave length band as a function of time after administration of the photo sensitizer(s).
4. If applicable, upon administration of further photo sensitizers emitting preferably in another wave length band and/or collecting in tissue of a different nature, the variation in emission (possibly over its development versus time) and/or the emission in the respective wave length bands is detected.
5. The condition of the respective irradiated tissue is determined on the basis of the differential signals between the individual emissions and/or the added signals in the individual emission bands, and tumour diagnosis is performed in particular.

It is also possible—instead of the (not necessarily) simultaneous stimulation of (at least) two fluorescence modes stimulated by two photo sensitizers—to stimulate (at least) one fluorescence mode stimulated by a photo sensitizer and (at least) one endogenic fluorescence mode and/or at least two endogenic fluorescence modes.

In the alternative at least one observation filter is provided for each of the fluorescence modes that can be stimulated, with the transmission characteristics of the filter(s) being matched with the respective fluorescence mode. With such an inventive device it is hence possible to stimulate at least two fluorescence modes simultaneously. The images associated with the respective fluorescence modes are separated by the appropriately structured filters in the path of the observation beam. The images can be processed, for instance in an image processing system, in an additive or subtractive form and/or be compared against the "standard image" on the basis of the directly reflected light.

In another alternative the transmission characteristics of the observation filter system, which may be composed of several filters if necessary, are so selected that all fluorescence modes which can be simulated may be observed simultaneously, without any change of the filter—possible in different or additional detection channels.

When the images obtained with the individual fluorescence modes are separated the observation filters for the individual fluorescence modes may be inserted successively into the observation beam path; it is also possible to arrange the individual filters in different partial beam paths.

In such a case the two partial beam paths may be formed, for instance, by performing a proximal splitting by means of a beam splitter which may be selective in terms of wave lengths in particular.

Moreover, the endoscope may be a stereo endoscope in which the different filters are provided in the stereo channels.

In the first case, it is preferable to provide a central filter-switching device for the observation filters because then the physician's attention will not be distracted by a comparatively complex switching procedure.

The switching device may be part of a communication system between the endoscope with filter changing device, the illuminating light source(s) and the video image receiver (s).

In all other respects, the device may be configured in a manner known per se.

It is possible, for example, that the image transmitter system transmits the image of the lens optically—e.g. via relay lens systems or imaging fibre bundles—to the proximal end of the endoscope. On the proximal end at least one video image receiver may be provided for receiving the proximal image of the image transmission system.

In an alternative, the image transmission system may comprise at least one distally disposed video image recorder for recording the image of the lens. In this case the image is "electrically" transmitted, i.e. by the transmission of the signals from the at least one image recorder.

It is preferred in any case that the device is suitable for application also for conventional diagnostic or treatment procedures, i.e. procedures not operating on fluorescence. To this end it is expedient that at least the observation filters can be removed from the observation beam path.

In another preferred embodiment of the invention the observation filters produce such an optical effect that they correct the chromatic aberration of the observation beam path.

BRIEF DESCRIPTION OF THE DRAWINGS

The invention will be described in more details in the following by an embodiment with reference to the drawing wherein.

DESCRIPTION OF AN EMBODIMENT

Figure 1:
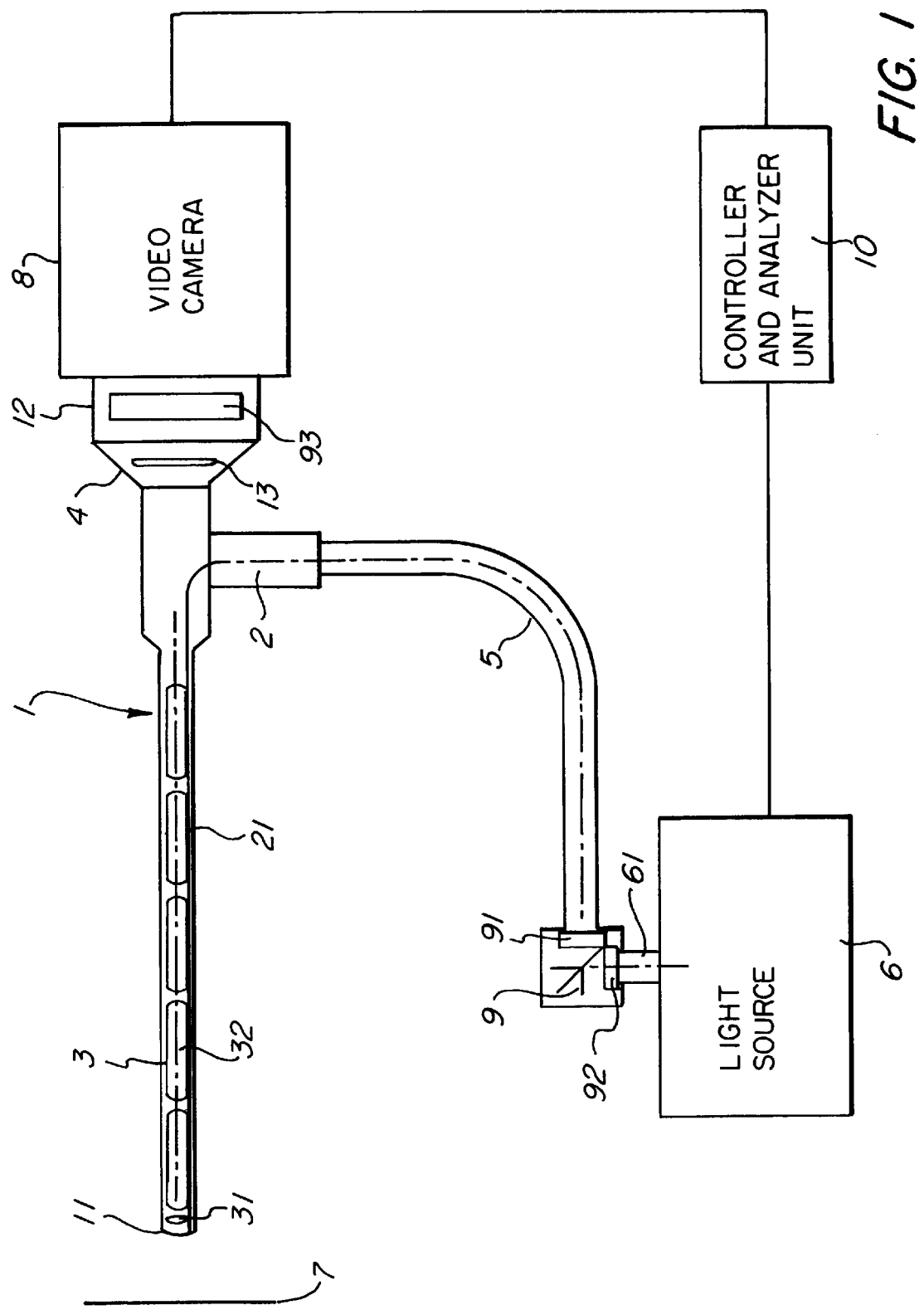
FIG. 1 is a schematic view of an inventive device for endoscopic applications.

FIG. 1 shows a schematic illustration of the structure of an inventive device for endoscopic applications. The basic structure is known from the document WO 97/11636 which explicit reference is made to with respect to the explanations of all particulars not described here in details. For other applications such as those in microscopy the configuration must be modified correspondingly.

The reference numeral 1 denotes an endoscope which may be a rigid or a flexible endoscope. The endoscope 1 comprises—in a manner known per se—a connector 2 for the optical guide, an elongate element adapted to be introduced into a human or animal body (not illustrated here), and an eyepiece 4 (in the illustrated embodiment).

The connector 2 for the optical guide of the endoscope 1 is connected via a flexible light guide 5 to a light source 6 which may comprise, for instance, a Xenon discharge tube. An optical guide 21, consisting of a fibre bundle, for instance, in the endoscope 1 passes the light from the light source 6, which is coupled into the connector 2 for the optical guide, to the distal end 11 of the endoscope. The light exiting from the distal end 11 illuminates a tissue region 7 to be examined and to be treated, if applicable.

The light arriving from the tissue region 7 enters a lens 31 on the distal end 11 of the endoscope 1, which is illustrated in a schematic form only. The image created in the image plane of the lens 31 (which plane is not identified in more details) is passed through an image transmitter 32 to the proximal end 12 of the endoscope. Then a—possibly enlarged or reduced—image of the tissue region 7 is created in the plane 13.

In the embodiment illustrated here, the image transmitter 32 comprises a plurality of relay lens systems whereof each implements 1:1 imaging and consists of so-called rod lens systems, as is known from rigid endoscopes. In an alternative, the image transmitter 32 may comprise a fibre imaging systems of the type common in flexible endoscopes.

In another alternative, which is not illustrated in FIG. 1, a video image recorder may be disposed in the image plane of the lens 31 so that an optical image transmission from the distal to the proximal end may be dispensed with.

The image of the tissue region 7, which is created in the proximal image plane 13—in the embodiment illustrated here—can be viewed with the eye through the eyepiece 4. Insofar the basic configuration is known, for instance from the D-Light system of Karl Storz GmbH & Co., Tuttlingen, Germany, as described in Endo World 17/1-D 997, which is explicitly referred to in all other respects for the explanations of all terms and particulars not described here in more details.

In the embodiment shown in FIG. 1 a filter housing 12 is flanged to the eyepiece 4, with a video camera 8 being mounted in its turn on this filter housing. The video camera 8 is provided with one or several image pick-ups which may be CCD image pick-ups in particular.

It is also possible to arrange, instead of an eyepiece, one or several image pick-ups in the image plane 13 directly or via intermediate images in a form conjugated with the image plane 13, as is equally known from prior art. Moreover, the image can be recorded simultaneously via a beam splitter with the video camera, in addition to viewing with the eyes.

Filter systems 91 and 92 or 93, respectively, are introduced into the illuminating beam path formed by the elements 6, 5, 2 and 21 and into the observation beam path formed by the elements 31 and 32, 4 and 8 for performing photo-dynamic diagnoses—as has been set out in the foregoing.

To this end, in the embodiment according to FIG. 1 a filter housing 9 is mounted on the light output port 61 of the light source 6, on which housing the fibre optic light guide is flanged. The filter system 9 comprises a thermally stable interference filter 91 and a thermally stable heat-absorbing filter which is substantially intended to reduce the thermal load on the interference filter 91.

A filter 93 is mounted between the eyepiece 4 and the video camera 8 in the filter housing 12. The filter 93 may be an element of a filter-changing means such as a filter turret in particular. The filter turret may be adapted to be controlled via a motor and/or provided with a sensor which communicates the position of the filter turret to the unit 10 which will be described in more details hereinbelow.

Explicit attention should be drawn to the fact that the illustrated arrangement of the filters 91 and 92 in the illumination beam path and the filter 93 in the observation beam path is only one possibility—even though a preferred one—while other arrangements at other locations are equally conceivable.

The exposure setting of the video camera 8 and the light emission from the light source 6 are controlled by the aforementioned controller and analyser unit 10 which can furthermore include also an image-processing unit.

Furthermore, the controller and analyser unit 10 is able to synchronise a flash light source in the light source 6 with the light integration phase of one or several CCD chips in the video camera 8. Moreover, the controller and analyser unit 10 can regulate the light output emitted from the light source 6 and/or the exposure setting of the video camera.

The output signal of the video camera 8 is also applied to the controller and analyser unit 10. The image processing unit in the analyser unit is suitable to process the output signal from the video camera in the manner defined in the Claims, which will be described in an exemplary manner in the following and to display the direct output signal and/or the signal obtained after image processing on (at least) one monitor—which is not illustrated in further details in FIG. 1. It is also possible, of course, to store the output signal received from the video camera directly and/or available after image processing, e.g. by means of a video recorder and/or in an image data base or to process it in any other way by electronic data processing techniques.

When one or several photo sensitizers are used both the reflected illuminating light and fluorescent light are emitted from the tissue region 7, with the fluorescent light being due to the light-induced reaction caused by the photo sensitizer and/or by endogenic fluorescence in biologic systems. In order to be able to detect the fluorescence light fraction, which is small in comparison against the amount of reflected light, and to separate it reliably from the "non-fluorescence light", particularly in a subsequent image processing step, an appropriately selected transmission characteristic of the illuminating and observation beam paths is required, in other words quasi an optical image pre-processing:

The filters 91 and 93, which can be inserted into the beam path, serve to set the transmission characteristic during the photo dynamic diagnosis. With the filters being adapted for removal by pivoting them out of the beam paths, for instance, also a normal observation of the tissue region 7 is possible without the potential occurrence of phenomena such as colour distortion.

The following is an exemplary explanation of the characteristic of the filters 91 and 93 for the case that delta amino levulinic acid is used as photo sensitizer. With the application of other photo sensitizers the filter characteristic must be appropriately adapted.

The starting point for the determination of the filter characteristics is the idea that the spectrum of an incoherent light source should be so configured that auto fluorescence endoscopy and endoscopy based on photo sensitizer fluorescence, for example, will be possible in addition to white-light endoscopy for achievement of a largely optimum result for tissue differentiation.

In the auto fluorescence mode the endoscopic image should be reproduced with the highest contrast possible with a colour reproduction approaching that of a white-light image. Moreover, the findings obtained in a possible photo sensitizer fluorescence examination should be combined with the auto fluorescence findings such that they will furnish a better result in the histographic typification of the tissue.

In accordance with the present invention one and the same stimulating filter 91 is used for stimulating at least two fluorescence modes, e.g. auto fluorescence and at least one photo sensitizer fluorescence. Moreover, two different observation filters 93 at maximum are used in the observation system.

For the auto fluorescence mode the filters 91 and 93 present the following characteristics:
  significant overlapping of the filter graphs of both filters only in the range 455–565 nm transmission of the stimulating filter 91:
    T (395–445 nm)
    >70%
    specifically >94%
    T (460–480 nm) >0.1%
    1%>T (540–700 nm) >0.95%
    transmission of the observation filter 93
    T(395–445 nm) <2%
    T(470–660 nm) >70%

The observation filter 93 presents a steep rise between 445 nm and 470 nm. The stimulating filter may present a "spur" in the range between 465 nm and 487 nm, which, together with the steep drop between 445–447 nm and 460 nm, leads to a significant overlapping of the filter graphs in this range.

When another photo sensitizer such as protoporphyrin IX is used instead of or additionally to ALA-5 the filter characteristics must be matched correspondingly.

It is moreover preferable to provide so-called filter switchers for both the stimulating filter 91 in the illuminating beam path and the fluorescence observation filter 93, which ensure a synchronised switching from a "master", e. g. the unit 10. At the same time it is preferred to make also provisions for colour weighting or colour matching, respectively, of the video camera.

The respective corresponding filters are pivoted into the observation beam path, and possible into the illuminating beam path, for the individual modes. These filter changes are synchronised either under electronic or manual control.

In order to facilitate the diagnosis for the examining physician the information appertaining to the different modes is preferably combined in a single image.

With 5-ALA/PPIX fluorescence it is possible to leave the fluorescence observation filter on the endoscope eyepiece 4 even during observation under white-light because the stimulation in the blue ranges takes place only within the range up to 430 nm approximately. With auto fluorescence, by contrast, almost the entire blue spectral fraction is blocked so that the natural colours are not reproduced with white-light observation using the observation filter. Hence a change by means of a filter switcher is expedient.

The present invention has so far been described by way of an example; however, the following features can also be implemented, as a matter of fact: Instead of the endoscope illustrated in FIG. 1 a stereo endoscope may be used which comprises a light feeder system and two separate observation channels. In the first channel the auto fluorescence observation filter may be integrated while the 5-ALA-PPIX observation filter may be integrated into the second channel.

When two different fluorescence signals (e.g. NADH and FLAVIN (FAD)) are recorded in different wavelength ranges one can obtain an improved information about the tissue state HEALTHY/TUMOUR EDGE/TUMOUR by different fluorescence signals of the two channels.

A filter housing 12, which can be detached from the endoscope 1, permits the application of the endoscope as standard white-light endoscope.

The observation filter 93 may be realised as a lens serving to correct the chromatic aberration of the endoscope transmission system.

Due to the separate fine tuning of the background light, e. g. in the blue spectral range, via a second light source emitting light which is coupled via a beam coupler into the light feeder channel, it is possible to perform additional examinations.

When, for instance, light having a wavelength of less than 370 nm (e. g. 355 nm) is coupled in it is possible to stimulate NADH fluorescence.

It is furthermore particularly preferred that a focussing means be provided in the light source 6 or in the light feeder channel 5 or 21, respectively, which permit a variation of the exit angle of the light emitted onto the object field 7 of the lens 31 so that when one and the same object is viewed more or less diffuse stimulating light will be emitted or that illuminating light comes from different directions:

This concept presents the advantage that artefacts due to irradiation and caused, for instance, by shadowing can be detected and will not be interpreted as tissue anomalies. When furthermore the same object is viewed the polarisation of the light can be varied via a polarising filter for equally detecting artefacts due to irradiation. It is an advantage if the emission angle variation or the polarisation, respectively, are synchronised with the video image frequency so that it will be possible, for instance, for an on-line image processing or image analysing unit to detect the differences in reflection or the differences in (auto) fluorescence on the same object.

This idea can also be appropriately implemented with a stereo endoscope. In such a case the light radiation were different already for both observation channels.

In video observation moreover the RGB signal can be evaluated or analysed in different ways:

It is possible, for instance, to exaggerate the blue fraction so that the image which is not induced by fluorescence radiation will clearly appear. Auto fluorescence occurs preferably in the green channel whilst fluorescence induced by medicaments occurs in the red channel.

The foregoing description of embodiments, which refers to the application of delta amino levulinic acid as photo sensitizer, does not restrict the general inventive idea which can be derived from the Claims and from the description.

What is claimed is:

1. A method for fluorescence diagnosis of tissue, including the steps of:
   providing an illuminating light source emitting light over a wide bandwidth;
   guiding light emitted from the illuminating light source along an illuminating beam path to illuminate the tissue;
   providing a stimulation filter system selected to transmit light from the illuminating light source in a stimulation wavelength range in which the light stimulates an emission of fluorescence light in at least two separate fluorescence wavelength ranges from fluorescent substances present in the tissue;
   inserting the stimulation filter system into the illuminating beam path;
   exposing the tissue to the light transmitted by the stimulation filter system to stimulate emission of the fluorescence light in the at least two separate wavelength ranges;
   guiding fluorescence light emitted from the tissue along an observation beam path;
   inserting into the observation beam path a first observation filter system selected to transmit fluorescence light having a first of the at least two separate fluorescence wavelength ranges which is emitted from the tissue and to substantially separate the transmitted fluorescence light from light in the stimulation wavelength range which is reflected from the tissue;
   inserting into the observation beam path instead of the first observation filter system a second observation filter system selected to transmit fluorescence light having a second of the at least two separate fluorescence wavelength ranges which is emitted from the tissue and to substantially separate the transmitted fluorescence light from light in the stimulation wavelength range which is reflected from the tissue; and
   forming a first image of the tissue with the fluorescence light from the first observation filter system;
   forming a second image of the tissue with the fluorescence light from the second observation filter system; and
   selectively observing the first and the second images.

2. A method according to claim 1, wherein the illuminating beam path passes through an endoscope from a proximal end to a distal end of the endoscope to illuminate the tissue.

3. A method according to claim 2, wherein fluorescence light emitted from the tissue is guided along an observation path passing from the distal end to the proximal end of the endoscope.

4. A device for fluorescence diagnosis of tissue comprising:
   an illuminating system having at least one illuminating light source for emitting light over a wide bandwidth;
   an illuminating beam path along which light emitted from the illuminating light source is guided to illuminate the tissue;
   a stimulation filter system inserted in the illuminating beam path and selected to transmit light from the illuminating light source in a stimulation wavelength range in which the light stimulates an emission of fluorescence light in at least two separate fluorescence wavelength ranges from a fluorescent substance present in the tissue;
   an observation beam path along which fluorescence light from the tissue is guided;
   a first observation filter system inserted in the observation beam path and selected to transmit fluorescence light having a first of the at least two separate fluorescence wavelength ranges which is emitted from the tissue and to substantially separate the transmitted fluorescence light from light in the stimulation wavelength range which is reflected from the tissue;
   a second observation filter system inserted in the observation beam path instead of the first observation filter system and selected to transmit fluorescence light having a second of the at least two separate fluorescence wavelength ranges which is emitted from the tissue and to substantially separate the transmitted fluorescence light from light in the stimulation wavelength range which is reflected from the tissue; and
   an imaging unit for forming a first and a second observable image of the tissue with the fluorescent light transmitted by the respective observation filter systems;
   wherein the first and the second images are selectively observable.

5. The device according to claim 4, comprising an endoscope, the illuminating beam path passing through the endoscope along a light guide from a proximal end to a distal end of the endoscope, and the observation beam path passing through the endoscope from the distal end to the proximal end, and an objective lens at the distal end of the endoscope forming a part of the imaging unit.

6. The device according to clam 5, wherein for endoscope fluorescence diagnosis the imaging unit comprises an image transmission system that transmits an image formed by the objective lens to the proximal end of the endoscope.

7. The device according to claim 6, wherein at least one video image pick-up means is provided at the proximal end of the endoscope to record the transmitted image.

8. The device according to claim 7, wherein the video image pick-up means comprises at least one CCD pick-up means.

9. The device according to claim 8, wherein the illuminating light source is a periodically operating flash discharge lamp with a flash exposure phase that is controlled by a controller and analyzer unit such that a flash exposure occurs exclusively during a light integration phase of the CCD pick-up means.

10. The device according to claim 9, wherein the illuminating system further comprises a continuously operating light source.

11. The device according to claim 8, wherein the video image pick-up means is provided with a variable exposure setting means.

12. The device according to claim 7, wherein an output signal of the video image pick-up means is applied to an image processing unit.

13. The device according to claim 12, wherein the image processing unit blocks out at least one hue range in a displayed multi-color image, and/or weights another hue range more strongly than remaining hue ranges.

14. The device according to claim 13, wherein the image processing unit activates and deactivates a channel for increasing contrast in RGB processing, the channel selected from the group consisting of blue or green.

15. The device according to claim 13, wherein the image processing unit superimposes a blocked out hue range in a shutter type manner onto a displayed multi-color image.

16. The device according to claim 12, wherein the image processing unit performs an HIS transformation.

17. The device according to claim 12, wherein the image processing system computes a contrast value for a maximum fluorescence wavelength at isolated locations of a displayed multi-color image for diagnosing possible tumors.

18. The device according to claim 6, wherein the image transmission system comprises at least one distally disposed video image pick-up means at the distal end of the endoscope for recording the image formed by the objective lens.

19. the device according to claim 5, wherein the observation beam path is split into at lest two partial beam paths, for which different observation filter systems are provided, by means of a beam splitter at the proximal end of the endoscope.

20. The device according to claim 19, wherein the beam splitter is an element selective in terms of wavelength or a polarizing splitter.

21. The device according to claim 5, wherein the light guide includes at least one fiber having a numerical aperture greater than 0.45.

22. The device according to claim 21, wherein a core of the at least one fiber is quartz and an envelope of the at least one fiber is of a thermally stable material.

23. The device according to claim 5, wherein a light-transmitting cross-sectional area of the light guide does not exceed 4 mm$^2$.

24. The device according to claim 5, wherein the illuminating light source is an endoscope light source.

25. The device according to claim 24, wherein a power consumption of the endoscope light source is at least 300 Watts.

26. The device according to claim 5, wherein a focusing means is provided in the illuminating light source or the illuminating beam path for varying an exit angle of light emitted from the illuminating light source.

27. The device according to claim 4, wherein transmission characteristics of the stimulation filter system are selected so that at least two fluorescent modes can be stimulated in the tissue, where one fluorescence mode is a fluorescence of a photo sensitizer and another fluorescence mode is an endogenous fluorescence of the tissue.

28. The device according to claim 27, wherein the following relationships are satisfied by a spectral transmittance T of the stimulation filter system in the stated wavelength ranges:

T (395 to 445 nm)>70%

5%>T (460 to 480 nm)>0.1%

T(540 t 00 nm)~0.05 to 0.1% for stimulating fluorescence induced by 5-amino levulinic acid (5-ALA) as photo sensitizer and endogenous fluorescence, and a significant overlap of spectral transmittance ranges of the stimulating filter system and the observation filter system occurs merely in a range from about 455 to about 465 nm.

29. The device according to claim 4, wherein transmission characteristics of the stimulation filter system are selected to so that at least two fluorescent modes can be stimulated in the tissue, which are fluorescences of different photo sensitizers.

30. The device according to claim 4, wherein transmission characteristics of the stimulation filter system are selected so that at least two fluorescent modes can be stimulated in the tissue, which are different endogenous fluorescences.

31. The device according to claim 4, wherein the observation filter systems for individual fluorescence wavelength ranges are adapted to be introduced successively into the imaging unit.

32. The device according to claim 31, wherein a central filter switching means is provided for switching between the first and the second observation filter systems.

33. The device according to claim 32, wherein the filter switching means constitutes part of a communication system which communicates information or control signals between the illuminating light source, and at least one video pick-up means.

34. The device according to claim 33, wherein the information or control signals set a mode of the video image pick-up means.

35. The device according to claim 34, wherein a control unit with a memory is provided for the video image pick-up means, which permits a reproduction of a previously stored setting for the respective fluorescence wavelength range selected.

36. The device according to claim 32, wherein the central filter switching means is mounted on an endoscope through which the illuminating beam path passes.

37. The device according to claim 32, wherein the central filter switching means is mounted on a filter turret.

38. The device according to claim 4, wherein the observation beam path is split into at least two partial beam paths for which different observation filter systems are provided.

39. The device according to claim 38, wherein the at least two partial beam paths pass through a stereo endoscope having two stereo channels provided with different observation filters.

40. The device according to claim 4, wherein the observation filter systems are removable from the imaging unit.

41. The device according to claim 4, wherein the stimulation filter system is removable from the illuminating beam path.

42. The device according to claim 4, wherein the observation filter systems and the stimulation filter system are removable from the imaging unit and the illuminating beam path, respectively, and a removal of the filter systems permits the imaging unit to form an image of the tissue illuminated by the light of the illuminating light source.

43. The device according to claim 42, wherein the image of the tissue is a normal image.

44. The device according to claim 42, wherein provision is made for removing the observation filter system and replacing the stimulating filter system by a filter system which permits visual observation of a tissue image having a natural color.

45. The device according to claim 44, wherein the filter system replacing the stimulating filter system has a transmission characteristic similar to that of the observation filter system.

46. The device according to claim 4, wherein a quantity of light incident on the tissue is adjustable without any variation of a color temperature of the illuminating light source.

47. The device according to claim 46, wherein an attenuator is provided in the illuminating beam path for setting the quantity of light.

48. The device according to claim 47, wherein the attenuator is selected from one of a grid and a grating.

49. The device according to claim 4, wherein an additional light as source is provided for illuminating the tissue to permit visual observation.

50. The device according to claim 4, wherein a plurality of light sources are provided, said illuminating light source emitting light over a wide bandwidth is a lamp system, and another light source is a laser system.

51. The device according to claim 4, wherein a plurality of light sources are provided, the light of which can be coupled into the illuminating beam path.

52. The device according to claim 4, where in a spectral transmittance of an overall system comprising,the illuminating beam path and the observation beam path is more than 5% in a wavelength range having an extent of 50 nm at maximum, and less than 5% in all other ranges within a visible wavelength region.

53. The device according to claim 4, wherein:
a spectral transmittance of the illuminating beam path has first pass bands in a fluorescence stimulation wavelength range of at least one fluorescent substance present in the tissue, and one second pass band in a wavelength range betweens the fluorescence stimulation wavelength range and the fluorescence wave length range;
a spectral transmittance of the observation beam path has a first pass band in a fluorescence wavelength range of the at least one fluorescent substance present in the tissue, and a second pass band in the same wavelength range as the second pass band of the illuminating beam path; and
a spectral transmittance of an overall system consisting of said illuminating beam path and said observation beam path has a transmittance of more than 5% only in said second pass band and less than 5% in all other wavelength ranges.

54. The device according to claim 4, wherein at least one of the first and second observation filter systems has an optical effect of correcting chromatic aberration in the observation beam path.

55. The device according to claim 4, wherein transmission characteristics of the illuminating system and the imaging unit are set so that a total intensity of fluorescence light is of a same order of magnitude as a total intensity of the light of the illuminating system which is directly reflected from the tissue.

56. The device according to claim 4, wherein the observation filter system comprises at least two filters adapted to be inserted into the illuminating beam path, where one of said filters is a thermally stable interference filter and the other of the filters is a thermally stable heat-absorbing filter.

57. The device according to claim 56, wherein the at least two filters have a substrate of a thermally resistant glass material.

58. The device according to claim 57, wherein the substrate is of quartz.

59. The device according to claim 4, wherein the illuminating light source comprises at least one gas discharge lamp.

60. The device according to claim 59, wherein the gas discharge lamp is a xenon lamp.

61. The device according to claim 59, wherein the gas discharge lamp is provided with an elliptical reflector having a light exit numerical aperture greater than 0.45 and giving a linear focus having a diameter of less than 2 mm.

62. The device according to claim 59, wherein the gas discharge lamp is provided with a parabolic reflector as well as a focusing lens system with at least one a spherical surface giving a linear focus having a diameter of less than 2 nm.

63. The device according to claim 4, wherein wavelengths of the stimulating light are variable.

64. The device according to claim 4, wherein the illuminating beam path and said observation beam path are integrated into a microscope.

65. The device according to claim 64, wherein the microscope is a microscope for neurosurgical or ophthalmologic examinations.

66. The device according to claim 4, wherein a state of polarization of the light stimulating an emission of fluorescence light is variable.

* * * * *

UNITED STATES PATENT AND TRADEMARK OFFICE
CERTIFICATE OF CORRECTION

PATENT NO.    : 6,510,338 B1
DATED         : January 21, 2003
INVENTOR(S)   : Klaus M. Irion et al.

It is certified that error appears in the above-identified patent and that said Letters Patent is hereby corrected as shown below:

<u>Title page,</u>
insert -- Item [64], Continuation of application No. PCT/DE99/00340, filed on February 8, 1999. --

Signed and Sealed this

Twenty-second Day of July, 2003

JAMES E. ROGAN
*Director of the United States Patent and Trademark Office*